United States Patent [19]

Munari et al.

[11] Patent Number: 4,863,871
[45] Date of Patent: Sep. 5, 1989

[54] METHOD AND DEVICE FOR ADJUSTING THE COOLING TEMPERATURE OF A SAMPLE TRAP IN AN APPARATUS FOR GAS CHROMATOGRAPHIC ANALYSIS

[75] Inventors: Fausto Munari; Giovanni Ostan, both of Milan; Bruno Tosi, Verano Brianza, all of Italy

[73] Assignee: Carlo Erba Strumentazione S.p.A., Italy

[21] Appl. No.: 81,574

[22] Filed: Jul. 31, 1987

Related U.S. Application Data

[63] Continuation of Ser. No. 810,996, Dec. 19, 1985, abandoned.

[30] Foreign Application Priority Data

Feb. 21, 1985 [IT] Italy ................ 19600 A/85

[51] Int. Cl.[4] ............................. G01N 30/02
[52] U.S. Cl. ................... 436/161; 55/386; 62/51.1; 422/89
[58] Field of Search ............ 55/20, 67, 386; 62/217, 62/514 R; 422/89; 436/161

[56] References Cited

U.S. PATENT DOCUMENTS

| | | | |
|---|---|---|---|
| 3,289,424 | 12/1966 | Shepherd | 62/217 |
| 3,724,169 | 4/1973 | Santeler | 55/20 |
| 3,850,004 | 11/1974 | Vander Arend | 62/514 R X |
| 3,926,800 | 12/1975 | Stephens | 55/67 X |
| 4,242,885 | 1/1981 | Quack et al. | 62/514 R X |
| 4,314,459 | 2/1982 | Rivoire | 62/514 R |
| 4,336,691 | 6/1982 | Burstein et al. | 62/514 R X |

Primary Examiner—Charles Hart
Attorney, Agent, or Firm—Lerner, David, Littenberg, Krumholz & Mentlik

[57] ABSTRACT

This invention concerns a method and a device to perform the adjustment of the cooling temperature of a trap for samples in an apparatus of gas chromatographic analysis. The method according to the invention is characterized in that the cooling fluid flow fed to the trap is adjusted by varying the vacuum caused by a suction device downstream the trap, which is capable of sucking the cooling fluid from a vessel upstream the trap itself.

The device according to the invention is characterized in that it comprises a suction means placed downstream the trap and connected by means of a first duct to an end of the trap itself, the other end of the trap being connected, by a second duct, to a vessel containing the refrigerating fluid.

11 Claims, 1 Drawing Sheet

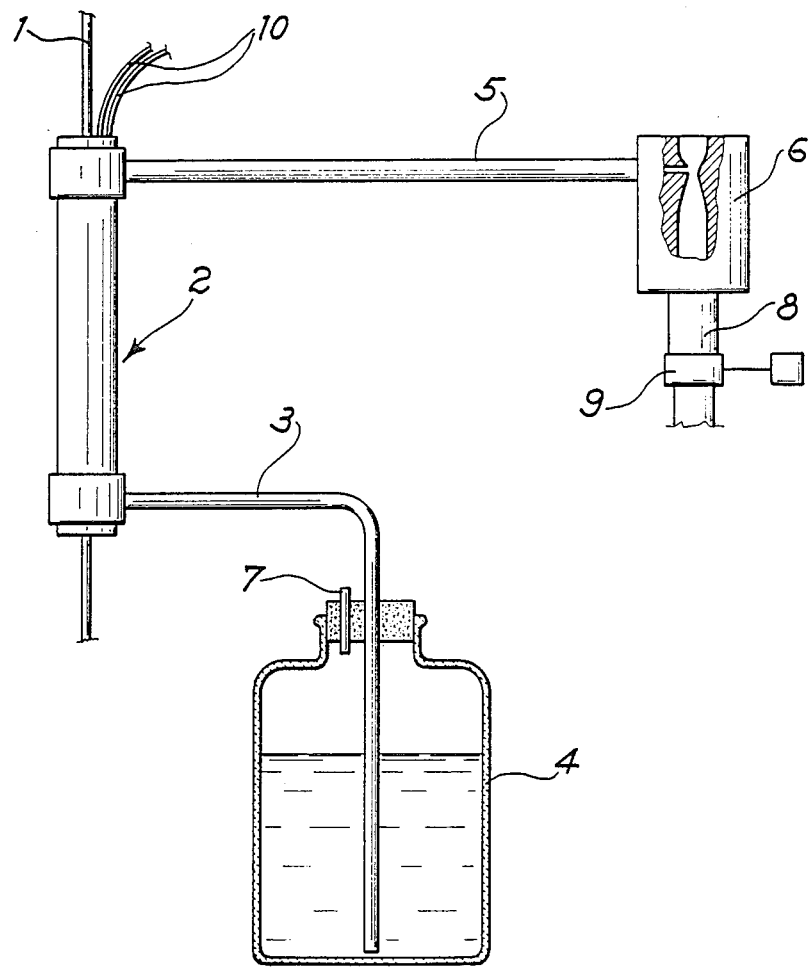

METHOD AND DEVICE FOR ADJUSTING THE COOLING TEMPERATURE OF A SAMPLE TRAP IN AN APPARATUS FOR GAS CHROMATOGRAPHIC ANALYSIS

This is a continuation of application Ser. No. 810,996, filed Dec. 19, 1985, now abandoned.

BACKGROUND OF THE INVENTION

1. Field of the Invention

This invention relates to gas chromatographic analysis equipments and concerns a method and a device to adjust the cooling temperature of a trap for samples to be analysed.

2. Description of the Prior Art

In equipments for gas chromatographic analysis so-called traps are used, which are placed along precolumns of gas chromatographic capillary columns, and whose main object is to perform the concentration of the sample to be analysed before it is forwarded along the column itself. Said traps are generally constituted by a metal jacket enclosing a section of pre-column or an initial section of gas chromatographic column. The concentration of the sample to be analysed is obtained by condensing the sample in said section of column or pre-column which is enclosed by the trap, through a cooling of the trap itself. The thus concentrated sample subsequently passes through the gas chromatographic column, when it is evaporated by heating the trap. Cooling is generally carried out by feeding a refrigerating fluid, preferably liquid nitrogen, into the hollow space existing between the column or the pre-column and the trap walls, while heating is generally obtained by Joule effect applying a potential difference at the two opposite ends of a resistor within the trap. Devices to feed nitrogen into the trap are known, comprising a vessel under pressure containing liquid nitrogen, a duct connecting the vessel with the trap and a solenoid valve opening and closing said duct.

Nitrogen feeding to the trap takes place thanks to the pressure existing within the vessel, the value of which is that of nitrogen vapor pressure.

In said known devices the adjustment of the trap cooling temperature can be performed exclusively by adjusting the opening time of the solenoid valve controlling the vessel/trap duct. In fact it is not possible to adjust the nitrogen flow to the trap with the necessary speed and precision by varying the pressure existing inside the vessel. For example a pressure increase could be obtained by heating the liquid nitrogen contained in the vessel or introducing a pressure gas, for instance helium, into the vessel itself. However both methods require too much time and are difficult to be controlled.

The adjustment of the nitrogen flow to the trap can be obtained also by varying the value of pressure losses along the vessel/trap duct, for instance using valves capable of supporting extremely low temperatures. Said valves however are very expensive and can be hardly used because ice tends to form on their electric contacts. As above said, the adjustment of nitrogen flow to the trap is generally obtained by varying the opening time of the solenoid valve controlling the vessel/trap duct. In order to make said regulation dependent only from the time, it is imperative to maintain the pressure inside the vessel at a constant value. For this reason the vessel is provided with a relief automatic device which restores the desired value of nitrogen vapour pressure when a temperature increase of liquid nitrogen, due to the unavoidable heat exchange between the vessel and the outside environment, causes a corresponding pressure increase.

Said regulation method however involves a first inconvenience due to the fact that between one opening of the valve and the following one it is necessary to wait that suitable balance conditions, under which the desired value of nitrogen vapour pressure is obtained, are restored within the vessel. This drawback strongly limits the use of said cooling devices in combination with so-called automatic samplers which automatically and in rapid succession perform the analysis of a large number of samples. Furthermore, each time that the vessel must be replaced for exhaustion of nitrogen, it is necessary to wait that in the new vessel the balance conditions are created again, which involves a suspension of analyses for a certain period of time. In order to reduce this drawback, large size vessels are generally used; however they are very expensive and cumbersome and impose heavy limitations to the allowed highest pressure value inside the vessel itself. Said limitation involves on its turn some inconvenience due to the fact that a low value of nitrogen vapour pressure inside the vessel makes it impossible to obtain a rapid cooling at very low temperatures of the trap. This is due particularly to the fact that, to have a regular flow of liquid nitrogen along the duct, it is necessary that the latter is brought to the temperature of liquid nitrogen itself, which requires some time.

On the other side, the difficulty of regulating the pressure of nitrogen fed to the trap makes it difficult to perform a precise regulation of the trap cooling temperature, mainly when relatively high (very near to 0° C.) temperatures have to be reached. In fact, in the latter case, the nitrogen flow rate, as determined by the pressure existing inside the vessel, causes a too rapid cooling to allow a control and a suspension thereof with the necessary precision and at the right time by the temperature recording system and by the system actuating the solenoid valve controlling the vessel/trap duct.

To overcome said drawback, the temperature of liquid nitrogen could be increased by mixing it with another gas before feeding it into the trap. Said method however involves the need of using a gas absolutely devoid of water (to avoid ice formation) and preferably without oxygen which condenses at the temperature of liquid nitrogen. Moreover said method does not allow accurate regulation of the cooling temperature of the trap.

The known devices, therefore, besides being extremely expensive, involve a series of drawbacks which make the adjustment of the cooling temperature of the trap very complicated and rough, with subsequent negative effects on the reliability of the results obtained from the analyses performed with the gas chromatographic equipment.

OBJECTS OF THE INVENTION

An object of this invention is therefore to provide a method and a related device which allow to obtain a precise adjustment of a trap cooling temperature both when it is necessary to perform a rapid cooling at very low temperatures and when it is necessary to perform a slow cooling at relatively high temperatures.

Another object of the invention is to provide a device for adjusting a trap cooling temperature, which results to be more simple and economic than those known up to now.

Still another object of the invention is to provide a device which allows to use a trap cooling apparatus reliably operating with automatic samplers.

SUMMARY OF THE INVENTION

Said objects are achieved by means of a method characterized in that the flow rate of refrigerating fluid to the trap, and therefore the trap cooling temperature, is adjusted varying the vacuum value produced by a suction device placed downstream the trap and capable of sucking the refrigerating fluid from a Dewar vessel which is placed upstream the trap itself.

The suction device is preferably a Venturi Tube and the adjustment of the refrigerating fluid flow rate to the trap is obtained by varying the working parameters of the Venturi tube itself. In particular, said adjustment can be obtained by varying the flow rate of a carrier fluid, for instance compressed air, fed to the Venturi tube by an on-off valve, by varying the pressure of said compressed air or by varying the efficiency of the Venturi tube.

One of the advantages of the method according to the invention lies in the fact that the refrigerating fluid flow rate to the trap is not linked to the pressure existing in the vessel containing the refrigerating fluid itself, so that the adjustment of said refrigerating fluid flow rate is much more simple and precise. Furthermore, as said adjustment is performed by indirectly acting on the refrigerating fluid through a sucking carrier fluid very easy to be handled, the whole cooling system of the trap is much more easy and economic. In particular, the refrigerating fluid can be contained in a conventional Dewar vessel at atmospheric pressure. The vessel in fact can be in communication with the outside environment through a vent.

Said latter feature makes the liquid nitrogen supply or Dewar vessel replacement operations extremely simple and allows to resume immediately the analyses once the vessel is filled or replaced.

The use of a Venturi tube as sucking means is particularly advantageous mainly when it is necessary to reach temperatures near to 0° C., when a very precise adjustment is necessary. In fact, the refrigerating fluid suction by a vacuum created inside a Venturi tube allows to obtain flow rates of said refrigerant fluid which are very reduced and suitable for a slow cooling at relatively high temperatures.

Further characteristics and features of the method and device according to the invention will be now described with reference to the accompanying drawing.

DESCRIPTION OF THE DRAWING

The only FIGURE of the drawing schematically illustrates a device for adjusting the temperature of a sample trap, according to the invention.

DESCRIPTION OF THE PREFERRED EMBODIMENT

With reference to the attached drawing, 1 indicates a pre-column or an initial section of a gas chromatographic column. A length of the pre-column or the gas chromatographic column 1 is enclosed by a trap 2 which is formed, in a way known in itself, by a jacket preferably made of stainless steel, sealingly closed on the column at its ends. The trap 2 thus forms a hollow space around the column 1 and within said hollow space there is provided an electric resistor for heating the trap and a thermocouple for recording the temperature inside the trap itself (conductors 10).

From each of the two ends of trap 2 a duct comes out; the bottom one 3, which is downstream in respect of the sample flow direction in column 1, ends in a vessel 4 containing the refrigerating fluid, preferably liquid nitrogen, while the top duct 5 comes out in correspondence of the narrow section of a Venturi tube 6. More in detail, the duct 3, which has a lower diameter than duct 5, draws on the bottom of vessel 4 which consists of a Dewar vessel communicating with the atmosphere through a vent 7. The Venturi tube 6 is fed for instance with air under pressure through a duct 8, controlled by a solenoid valve 9 of the on-off type. The solenoid valve 9 is actuated, in a way known in itself, by a thermoregulator (not shown) comprising a thermocouple housed in the trap and a device for reading the temperature values taken by said thermocouple and comparing said values with the desired ones.

A first adjustment of the cooling temperature of trap 2 is therefore performed by means of the solenoid valve 9 which controls the compressed air flow rate to the Venturi tube and indirectly adjusts the nitrogen feeding to trap 2. In particular, when inside the trap 2 a desired cooling temperature is reached, the solenoid valve 9 cuts off the compressed air fed to said Venturi tube 6, thus disconnecting the nitrogen flow to the trap. During the sample condensation step inside the column section surrounded by the trap, the solenoid valve resets the compressed air flow to the Venturi tube 6 each time the trap temperature raises above a desired value.

A second cooling temperature adjustment of trap 2 can be performed by adjusting the pressure value of the air fed to the Venturi tube. In fact, the higher the value of said pressure is, the higher is the sucking effect of Venturi tube on the nitrogen contained in vessel 6 and, consequently, the higher is the nitrogen flow rate to the trap 2. Of course, when the pressure value of air fed to Venturi tube decreases, the sucking effect exerted by said Venturi tube on nitrogen decreases as well and, consequently, the nitrogen flow rate to trap 2 decreases. The extremely simple and precise adjustment which it is possible to perform on the compressed air flow to the Venturi tube allows to obtain an equally simple and precise adjustment of the nitrogen flow fed to trap 2 and therefore of the trap cooling temperature. In particular, said adjustment allows to obtain very quick coolings at very low temperatures (approximately $-150°$ C.) as well as slow coolings at relatively high temperatures (approximately $-15°$; $-20°$ C.).

A further possibility of adjusting the cooling temperature of trap 2 can be obtained by varying the efficiency of said Venturi tube, for instance by varying the area of the minimum section for compressed air flow. The latter two adjustments of the nitrogen flow fed to the trap can be both set before the analysis, so that the suction produced by said Venturi tube is always the same for all samples to be analysed, or automatically varied for each sample to be analysed, in such a way that the cooling parameters are time by time those necessary for the particular sample under analysis.

We claim:

1. A method of adjusting the cooling temperature of a trap encasing at least a portion of a gas-chromatographic column or pre-column for the analysis of samples therein comprising maintaining a refrigerating fluid in a refrigerating fluid vessel substantially at atmospheric pressure, feeding said refrigerating fluid to said trap from said refrigerating fluid vessel through a valve-free conduit at a predetermined feed rate, drawing said refrigerating fluid through said trap solely by applying suction to said trap from a location downstream from said trap, whereby said suction acts directly on said refrigerating fluid through said valve-free conduit, and varying the degree of said suction so as to adjust said predetermined feed rate at which said refrigerating fluid is fed into said trap for adjusting the cooling temperature therein and thereby cooling said gas-chromatographic column.

2. The method of claim 1 wherein said varying of the degree of said suction comprises controlling the flow through a Venturi tube.

3. A device for adjusting the cooling temperature of a trap encasing at least a portion of a gas-chromatographic column or pre-column for the analysis of samples therein comprising a vessel for a refrigerating fluid, means for maintaining said vessel substantially at atmospheric pressure, feeding means for feeding said refrigerating fluid to said trap from said vessel at a predetermined feed rate, said feeding means comprising a valve-free conduit directly connecting said refrigerating fluid to said trap, conduit means for directing said refrigerating fluid to a location downstream of said trap, and suction means for creating a vacuum in said conduit means whereby said refrigerating fluid is drawn directly into said trap from said vessel through said valve-free conduit at said predetermined rate thereby.

4. The device of claim 3 including vacuum varying means for varying said vacuum created by said suction means so as to adjust said predetermined feed rate at which said refrigerating fluid is fed into said trap for adjusting said cooling temperature thereby.

5. The device of claim 4 wherein said vessel comprises a Dewar vessel including vent means for communicating with the atmosphere.

6. The device of claim 4 wherein said suction means comprises a Venturi tube including a throat, said conduit means is connected to said throat of said Venturi tube, and wherein said vacuum varying means includes working fluid delivery means for delivering a working fluid through said Venturi tube.

7. The device of claim 6 wherein said working fluid comprises compressed air, and wherein said vacuum varying mean sincludes solenoid valve means.

8. The device of claim 7 including thermocouple means within said trap, and including control means for controlling said solenoid valve in response to temperature values recorded by said thermocouple means.

9. A device according to claim 6 wherein said working fluid comprises a compressed working fluid at a predetermined pressure, and including pressure varying means for varying the pressure of said compressed working fluid thereby.

10. A device according to claim 7 including Venturi tube control means for controlling the suction created by said Venturi tube.

11. The device of claim 10 wherein said Venturi tube control means includes adjustment means for adjusting the size of said throat of said Venturi tube.

* * * * *